United States Patent
Bartal et al.

(10) Patent No.: US 8,315,452 B2
(45) Date of Patent: Nov. 20, 2012

(54) METHOD AND DEVICE FOR OBTAINING A VOLUME DATA SET OF A MOBILE TISSUE OR ORGAN OF A PATIENT

(75) Inventors: Meir Bartal, Zichron Yaakov (IL); Jan Boese, Eckental (DE); Assaf Govari, Haifa (IL); Matthias John, Nürnberg (DE); Assaf Preiss, Shimshit (IL); Norbert Rahn, Forchheim (DE)

(73) Assignee: Siemens Aktiengesellschaft, München (DE)

( * ) Notice: Subject to any disclaimer, the term of this patent is extended or adjusted under 35 U.S.C. 154(b) by 563 days.

(21) Appl. No.: 12/518,123

(22) PCT Filed: Apr. 4, 2008

(86) PCT No.: PCT/EP2008/054076
§ 371 (c)(1),
(2), (4) Date: Jun. 8, 2009

(87) PCT Pub. No.: WO2008/122599
PCT Pub. Date: Oct. 16, 2008

(65) Prior Publication Data
US 2010/0104164 A1    Apr. 29, 2010

(30) Foreign Application Priority Data
Apr. 10, 2007  (DE) .......................... 10 2007 016 902

(51) Int. Cl.
*G06K 9/00* (2006.01)
(52) U.S. Cl. ..................................................... 382/131
(58) Field of Classification Search ............. 382/128, 382/131, 154; 378/4, 8, 20
See application file for complete search history.

(56) References Cited

U.S. PATENT DOCUMENTS

| | | | |
|---|---|---|---|
| 2003/0058999 A1 | 3/2003 | Mitschke et al. | 378/207 |
| 2003/0152195 A1 | 8/2003 | Hebecker et al. | 378/162 |
| 2003/0179856 A1 | 9/2003 | Mitschke et al. | 378/205 |

(Continued)

FOREIGN PATENT DOCUMENTS

DE        10202091 A1    8/2003

(Continued)

OTHER PUBLICATIONS

Movassaghi et al., "3D Coronary Reconstruction from Calibrated Motion-Compensated 2D Projections Based on Semi-Automated Feature Point Detection", Proceedings of SPIE—The International Society for Optical Engineering, Bellingham, WA, Feb. 16, 2004, pp. 1943-1950, XP007904504,. vol. 5370, Nr. 1.

*Primary Examiner* — Andrew W Johns

(57) ABSTRACT

A method and a device for obtaining a volume data set of a mobile tissue or organ of a patient by a C-arm X-ray device are provided. An electromagnetic sensor of a position detection system is arranged indirectly on the tissue or organ. The X-ray device obtains a plurality of X-ray projections from the tissue or organ from various projection directions. A first method consists of reconstructing a volume data set from the X-ray projections, in which the electromagnetic sensor adopts a position characterizing a displacement phase of the tissue or organ. A second method consists of reconstructing a volume data set from the X-ray projections captured when the electromagnetic sensor was located in a position characterizing a displacement phase of the tissue or organ. A third method does not capture an X-ray projection for the reconstruction if the electromagnetic sensor is located in a position characterizing a displacement phase.

20 Claims, 2 Drawing Sheets

U.S. PATENT DOCUMENTS

| | | | |
|---|---|---|---|
| 2005/0119560 A1* | 6/2005 | Mostafavi | 600/425 |
| 2006/0064006 A1 | 3/2006 | Strommer et al. | 600/415 |
| 2006/0116571 A1 | 6/2006 | Maschke et al. | 600/424 |
| 2006/0215816 A1 | 9/2006 | Sandkamp et al. | 378/114 |
| 2006/0241372 A1 | 10/2006 | Nekovar et al. | 600/407 |
| 2007/0030945 A1 | 2/2007 | Boese et al. | 378/8 |
| 2008/0089465 A1* | 4/2008 | Teramoto | 378/12 |
| 2008/0218510 A1 | 9/2008 | Grass et al. | 345/419 |
| 2009/0116719 A1 | 5/2009 | Jaffray et al. | 382/131 |

FOREIGN PATENT DOCUMENTS

| | | |
|---|---|---|
| DE | 10206190 A1 | 9/2003 |
| DE | 10140867 B4 | 8/2005 |
| DE | 102004058008 A1 | 6/2006 |
| DE | 102005014286 A1 | 10/2006 |
| DE | 102005016472 A1 | 10/2006 |
| WO | WO 2007/015181 A1 | 2/2007 |
| WO | WO 2007/136967 A2 | 11/2007 |

* cited by examiner

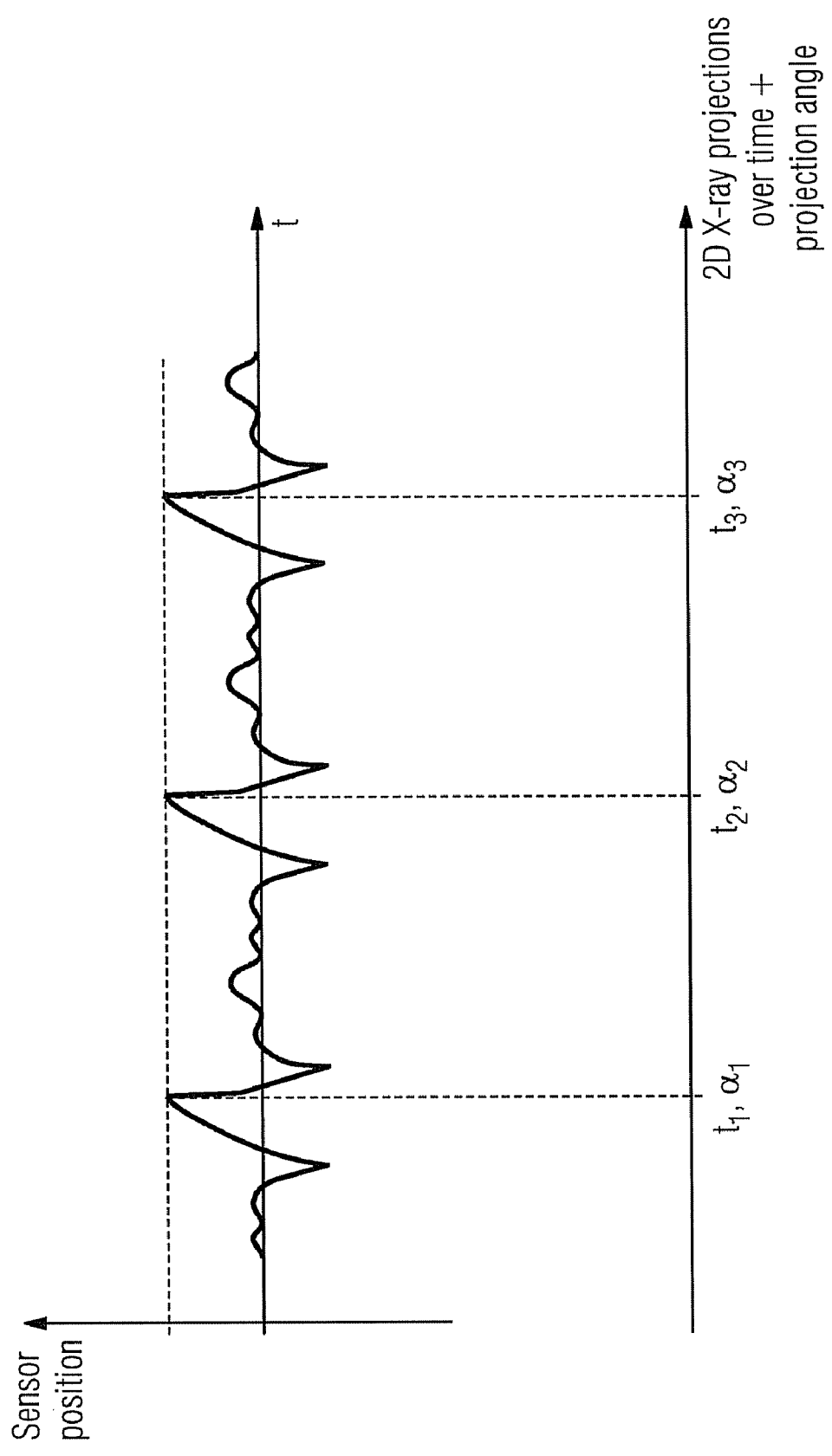

METHOD AND DEVICE FOR OBTAINING A VOLUME DATA SET OF A MOBILE TISSUE OR ORGAN OF A PATIENT

CROSS REFERENCE TO RELATED APPLICATIONS

This application is the US National Stage of International Application No. PCT/EP2008/054076, filed Apr. 4, 2008 and claims the benefit thereof. The International Application claims the benefits of German application No. 10 2007016902.9 filed Apr. 10, 2007, both of the applications are incorporated by reference herein in their entirety.

FIELD OF THE INVENTION

The invention relates to a method and to a device for obtaining a volume data set of a mobile tissue or organ of a patient by means of a C-arm X-ray device and an electromagnetic position detection system.

BACKGROUND OF THE INVENTION

A system consisting of a C-arm X-ray device and an electromagnetic position detection system, which position detection system may be additionally configured as a mapping system, is used for example for punctures, general catheter applications or catheter applications in the heart of a patient, the puncture needle or the catheter being navigated and/or guided in the patient on the basis of images of the patient obtained by the C-arm X-ray device and on the basis of position data of the puncture needle or of the catheter obtained by the electromagnetic position detection system and mapping system, by, for example, an image of the puncture needle or of the catheter being superimposed on the images obtained by the C-arm X-ray device. The electromagnetic position detection system and mapping system and the C-arm-X-ray device and/or the electromagnetic position detection system and mapping system and the images obtained by the C-arm-X-ray device are, to this end, generally registered with one another so that an image of the puncture needle or of the catheter may be superimposed on the X-ray images.

When treating cardiac arrhythmia of a patient by so-called ablation, an ablation catheter is inserted via veins or arteries into one of the heart chambers of the patient, for example by means of X-ray images obtained by the C-arm-X-ray device, and the tissue causing the cardiac arrhythmia is removed by high frequency current. A prerequisite for successfully performing a catheter ablation is, on the one hand, the accurate localization of the cause of the cardiac arrhythmia in the heart chamber and, on the other hand, the targeted removal of the tissue causing the cardiac arrhythmia. The tissue is located in an electrophysiological examination, in which electric potential is detected in a localized manner by a mapping catheter inserted into the heart chamber. From this electrophysiological examination, so-called electroanatomical mapping, 3D mapping data of the heart chamber is obtained, for example, which may be visualized on a monitor. The mapping function and the ablation function are, moreover, frequently combined in one catheter so that the mapping catheter is also at the same time an ablation catheter.

A known electroanatomical 3D mapping method, as may be carried out for example by the CARTO system of Biosense Webster Inc., USA, is based on an electromagnetic principle. By means of transmitters arranged beneath a patient positioning device, generally three different electromagnetic fields of low intensity are created. By means of electromagnetic sensors integrated in the catheter tip of the mapping catheter, it is possible to measure the voltage variations within the electromagnetic fields induced by the catheter movements, and by means of mathematical algorithms it is possible to calculate the position of the mapping catheter at any time. By specifically scanning the contour of a heart chamber by the mapping catheter while simultaneously detecting the electrical signals of the sensors, the mapping data is thus obtained and/or an electroanatomical three-dimensional map is produced.

The ablation catheter may, therefore, not only be guided by means of the above-mentioned X-ray images, but also using the electroanatomical mapping data. The X-ray images specifically do not show the anatomy of the patient, in particular the anatomy of the heart of the patient, in detail. A 3D view of anatomical details of the heart could increase the accuracy when carrying out the ablation as regards the morphology of the heart tissue, accelerate the implementation of the ablation and lead to a reduction of the X-ray radiation dose applied to a patient during an ablation.

In complex cases in particular, electrophysiologists welcome being able to carry out the ablation using a combination of electrophysiological and morphological criteria. For the electrophysiologists, therefore, it would be helpful to have available a combined visualization of 3D image data obtained by an imaging device and electroanatomical 3D mapping data.

The reconstruction of a volume data set of the heart of a patient using X-ray projections recorded by a C-arm X-ray device is generally EKG-triggered. Thus from DE 10 2005 016 472 A1, an operating method for an X-ray unit is known in which an X-ray arrangement is repeatedly pivoted between two end positions about a pivot axis. The X-ray arrangement is thus controlled so that, respectively in a plurality of angular positions at detection times, X-ray projections of a mobile object to be examined, which is arranged in the region of the pivot axis, are detected and supplied to a control device which stores the X-ray projections and the corresponding angular positions. The control device also receives an EKG signal relative to the object to be examined, and assigns information corresponding to a phase position of the object to be examined to each stored projection. For the reconstruction of a volume data set, the control device selects those X-ray projections in which the phase position at least approximately corresponds to a reconstruction phase position.

If the patient has cardiac arrhythmia, this form of EKG triggering however, is frequently not ideally suited for generating a volume data set of the heart of the patient which is free of smudges and/or motion artefacts which are produced by the cardiac arrhythmia.

SUMMARY OF THE INVENTION

The object of the invention, therefore, is to provide a method and a device of the aforementioned type by which a volume data set of the highest possible quality may be obtained of a mobile tissue or organ of a patient.

According to the invention, this object is achieved by methods for obtaining a volume data set of a mobile tissue or organ of a patient by a C-arm X-ray device and an electromagnetic position detection system as claimed in the claims.

According to the first method according to the invention, at least one X-ray positive electromagnetic sensor of the electromagnetic position detection system or an electromagnetic sensor of the position detection system provided with an X-ray positive marker, is arranged at least indirectly on the tissue or organ, the C-arm of the C-arm X-ray device, provided with an X-ray radiation source and an X-ray radiation receiver, being displaced around the patient for recording a plurality of X-ray projections of the tissue or organ of the patient from various projection directions. The X-ray positive electromagnetic sensor or the electromagnetic sensor provided with an X-ray positive marker is manually or automatically detected in the individual X-ray projections by a method of pattern recognition, and a volume data set is reconstructed based on those X-ray projections in which the X-ray positive electromagnetic sensor or the electromagnetic sensor provided with an X-ray positive marker, essentially adopts a position characterizing a displacement phase determined of the tissue or organ.

The electromagnetic sensor arranged on the mobile tissue or organ moves according to the tissue or organ and is imaged in each X-ray projection image. Based on the trajectory of the electromagnetic sensor which may be derived from all the X-ray projections, a specific position of the electromagnetic sensor which corresponds to a displacement phase determined of the tissue or organ may be selected and taking into account the respective projection angle the X-ray projections may be used for the reconstruction of the volume data set, in which the electromagnetic sensor has at least essentially adopted the position determined which characterizes the relevant displacement phase determined of the tissue or organ. For establishing the position determined of the electromagnetic sensor and thus for establishing the displacement phase determined of the tissue or organ, initially by using substantially all the X-ray projections, a volume data set may be reconstructed which, although comprising smudges, primarily illustrates the trajectory of the electromagnetic sensor. Based on this trajectory, as already mentioned, the relevant displacement phase may be established and those X-ray projection images which have been recorded substantially in this displacement phase may be selected. Generally, it will thus be necessary to displace the C-arm of the C-arm X-ray device repeatedly around the patient, in particular the mobile tissue and/or organ of the patient, possibly alternately with the recording of X-ray projections, in order to have sufficient X-ray projections available in the displacement phase of the tissue or organ from various projection directions for reconstructing the volume data set.

According to the second method according to the invention, the positions of the electromagnetic sensor are detected by the electromagnetic position detection system, and a volume data set is reconstructed based on those X-ray projections which have been recorded at the time when the electromagnetic sensor was essentially located in a position characterizing a displacement phase determined of the tissue or organ. The C-arm X-ray device and/or the recording of the X-ray projections by the C-arm X-ray device and the destination of the positions of the electromagnetic sensor by the electromagnetic position detection system are thus always synchronized in temporal terms when an X-ray projection is recorded, the position of the electromagnetic sensor being detected and preferably being assigned to the respective X-ray projection. The positions of the sensors may be detected, for example, relative to a coordinate system assigned to the electromagnetic position detection system. From all the position information of the sensor, a displacement curve of the electromagnetic sensor over time is also obtained, using which a determined displacement phase of the tissue or organ is able to be selected. Subsequently, the X-ray projection images belonging to this displacement phase are used for the reconstruction of the volume data set, the relevant X-ray projection images, for example, being able to be identified by their recording time when the electromagnetic sensor has respectively adopted the position characterizing the selected determined displacement phase.

According to the third method according to the invention, the positions of the electromagnetic sensor are detected by the electromagnetic position detection system and the C-arm of the C-arm X-ray device provided with an X-ray radiation source and an X-ray radiation receiver is displaced around the patient for obtaining a plurality of X-ray projections of the tissue or organ of the patient from various projection directions, an X-ray projection being recorded for the reconstruction of the volume data set only if the electromagnetic sensor is located in a position characterizing a determined displacement phase. In this case, therefore, the displacement curve of the electromagnetic sensor over time is detected by the electromagnetic position detection system and based on the displacement curve of the electromagnetic sensor a determined displacement phase of the tissue or organ is selected. Finally, during the displacement of the C-arm around the tissue or organ an X-ray projection is always triggered when the electromagnetic sensor is at least essentially located at the position determined.

Even in the case of the two alternate methods, the C-arm of the C-arm X-ray device generally has to be repeatedly displaced around the patient in order to provide sufficient X-ray projections from various projection directions for the reconstruction of a volume data set in the selected displacement phase of the tissue or organ.

It is common to all inventive methods that they are more suitable than conventional methods with regard to the triggering or the gating of the X-ray projection images, in particular for patients who suffer from cardiac arrhythmia, as by means of the electromagnetic sensor, even the smallest movements of the mobile tissue or organ may be detected, measured and correspondingly taken into account.

According to a variant of the invention, the mobile tissue or organ is the heart or the lungs of a patient.

According to one embodiment of the invention, the C-arm X-ray device and the electromagnetic position detection system are registered with one another. "Registering" is understood as the C-arm. X-ray device and the electromagnetic position detection system being aligned relative to one another in a defined manner and alterations to the position of the one device or system or components of the one device or system being communicated or made available to the other device or system.

According to a variant of the invention, the registering of the C-arm X-ray device and the electromagnetic position detection system with one another includes the determination of a coordinate transformation between an image coordinate system assigned to the C-arm X-ray device and a coordinate system assigned to the position detection system, using at least one X-ray positive electromagnetic body sensor arranged on the surface of the body of the patient or using at least one electromagnetic body sensor of the electromagnetic position detection system, arranged on the surface of the body of the patient and provided with an X-ray positive marker, which may be detected both in the X-ray projections or in the volume data set and by the position detection system. Generally, the coordinate transformation is determined by using three or more electromagnetic body sensors. Based on the coordinate transformation, in particular, positions of the electromagnetic sensors of the electromagnetic position detection system may be transformed into the image coordinate system and/or into images recorded by the C-arm X-ray device.

According to a further embodiment of the invention, the C-arm X-ray device and the position detection system are connected to one another via at least one data interface, via which the X-ray device and the position detection system may exchange position data with one another. In this manner, the electromagnetic position detection system always has access to position information of the X-ray device, in particular of the Also the C-arm X-ray device always has access to position information of electromagnetic sensors and/or position sensors of the electromagnetic position detection system.

One variant of the invention, by taking into account the projection direction of an X-ray projection and based on the position which the X-ray positive electromagnetic sensor or the electromagnetic sensor provided with an X-ray positive marker has adopted during this X-ray projection, provides for an image of the X-ray positive electromagnetic sensor or of the electromagnetic sensor provided with an X-ray positive marker to be superimposed on the respective X-ray projection. This projective superimposition of an image of the electromagnetic sensor may, in particular, facilitate the detection of the electromagnetic sensor in the X-ray projection images which may be performed manually or even automatically. The superimposition may also be used for monitoring purposes with regard to the second and third method according to the invention, for which the electromagnetic sensors used here have to be X-ray positive or provided with an X-ray positive marker.

According to one embodiment of the invention, based on the positions of the X-ray positive electromagnetic sensor or the electromagnetic sensor provided with an X-ray positive marker, and the X-ray projection images and/or based on the electromagnetic body sensor imaged in the X-ray projection images, or the electromagnetic body sensor provided with an X-ray positive marker, the projection matrices of the C-arm X-ray device are determined again. Generally, the projection matrices of the C-arm X-ray device are determined by a phantom in a calibration process before the start-up of the C-arm X-ray device, the knowledge of the projection matrices being necessary in order to be able to reconstruct a volume data set from a plurality of X-ray projections recorded from various projection directions. The determination of the projection matrices, which contain the projection geometries of the C-arm X-ray device, is in this case necessary as the C-arm per se is not an absolutely rigid mechanical system, but when displacing the C-arm around a patient or an object to be examined, mechanical deformation, effects of gravitational force, distortion of the C-arm, etc. occur. Thus for each C-arm X-ray device the projection matrices have to be determined in a calibration process and stored in a retrievable manner for the subsequent reconstruction of volume data sets of objects. According to the variant of the invention mentioned above, the projection matrices which are based on the positions of the electromagnetic sensor and the X-ray projection images and/or based on the body sensor imaged in the X-ray projection images, are determined again when measuring a patient. This provides the possibility of verifying the originally projection matrices determined.

A variant of the invention, therefore, provides for the correction of the projection matrices of the C-arm X-ray device by the recently determined projection matrices in the event of significant alterations which may be detected and the use for the reconstruction of a volume data set or the use of only recently determined projection matrices for the reconstruction of a volume data set.

According to a further variant of the invention, EKG signals are recorded by means of an EKG device, or data relevant to the respiration cycle is additionally recorded by a device for recording the respiration cycle, which may be used as additional information. The EKG signals or the signals relevant to the respiration cycle may also be used when the mobile tissue or organ exhibits a regular rhythm or cycle over a time period. In this regard, a combined application results. The EKG signals and/or the data relevant for the respiration cycle are thus made available to the C-arm X-ray device and/or the position detection system.

The object relating to the device is achieved by a device comprising a C-arm X-ray device, an electromagnetic position detection system and at least one computational device which is designed to execute a method described above. The electromagnetic position detection system is in this case preferably arranged in a defined manner on a patient positioning device, the C-arm X-ray device and the patient positioning device preferably being arranged in a defined manner relative to one another.

BRIEF DESCRIPTION OF THE DRAWINGS

An embodiment of the invention is shown in the accompanying schematic drawings, in which:

FIG. 1 shows a device according to the invention for carrying out the method according to the invention and FIG. 2 show a displacement curve of the electromagnetic sensor over time.

DETAILED DESCRIPTION OF THE INVENTION

Figure 1:
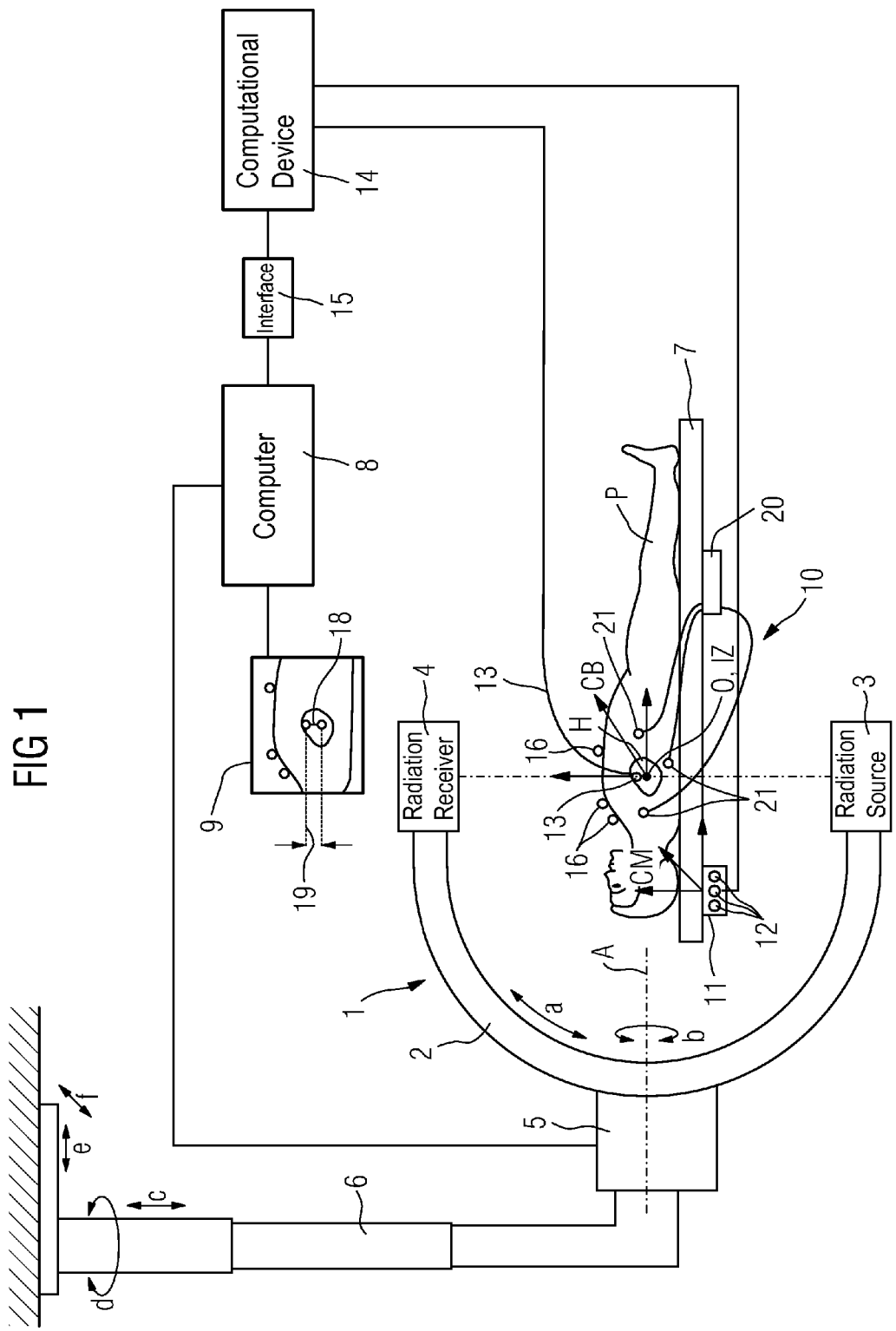

The device according to FIG. 1 comprises a C-arm X-ray device 1 comprising a C-arm 2, on which an X-ray radiation source 3 and an X-ray radiation receiver 4 are arranged opposing one another. A central beam of an X-ray radiation bundle emitted from the X-ray radiation source 3 extends in this case at least substantially through the isocenter IZ of the C-arm 2 and impinges at least approximately centrally on the input window of the X-ray radiation receiver 4. The C-arm 2 is displaceable mounted on a stand 5 about its orbital axis O in the directions of the double arrow a. The stand 5 is, in the case of the present embodiment, arranged on a ceiling stand, which provides the possibilities for displacement denoted in the figures by the double arrows c, d, e and f, of the stand 5 provided with the C-arm 2. Moreover, the C-arm 2 is able to be displaced with the stand 5 about its angulation axis A in the directions of the double arrow b.

The C-arm X-ray device 1 has a plurality of position measuring devices, not shown, by which alterations to the position of components of the C-arm X-ray device 1 are detected, one respective current position of a component of the C-arm X-ray device 1 being present in the computer 8 of the C-arm X-ray device 1. If, for example, the C-arm 2 is displaced about its orbital axis O in one direction of the double arrow a, this is detected by the position measuring device and the current position of the C-arm 2 is present in the computer 8 of the C-arm X-ray device 1. The same occurs with displacements of the stand 5, the ceiling stand 6 or other components of the C-a X-ray device 1.

In a manner known per se, by means of the C-arm X-ray device 1, 2D X-ray projections of a patient P positioned on a patient table 7 may be recorded from various projection directions. The C-arm X-ray device 1 and the patient table 7 are arranged and/or aligned relative to one another in a defined manner and registered with one another. Alterations to the position of the patient table 7, whether height adjustments or horizontal pivoting about a vertically extending axis, not shown, are also detected, for example via position measuring devices, and are available to the computer 8 via a connection, not shown.

The C-arm X-ray device 1 and the patient table 7 provided with the patient P are preferably aligned relative to one another for obtaining 2D X-ray projections of a relevant tissue area of the patient P, such that the relevant tissue area comes to rest at least approximately in the isocenter V, of the C-arm X-ray device 1.

In the case of the present embodiment, a volume data set is intended to be produced of the heart H of the patient P. To this end, by means of the C-arm X-ray device 1 a plurality of 2D X-ray projections of the heart H of the patient P have to be recorded from various position directions, in order to be able to reconstruct therefrom a volume data set of the heart H of the patient P. The reconstruction takes place in the case of the present embodiment by means of the computer 8 of the C-arm X-ray device 1, to which projection matrices which have been previously determined therefor in a calibration process and which contain the projection geometries of the C-arm X-ray device 1, are made available.

As the heart H of the patient P is a mobile organ, the movement of the heart has to be taken into account during the reconstruction of the volume data set in order to be able to obtain a high quality volume data set of the heart, free from image smudging, in particular in a specific cardiac phase, from which 3D images of the heart H are able to be produced in the specific cardiac phase of the patient P and shown on a monitor 9.

Hitherto, the movements of the heart H and/or the cardiac phases have been determined by an EKG device 20, to which EKG electrodes 21 are connected, in an EKG (electrocardiogram). The EKG electrodes 21 are in this case arranged on the surface of the body of the patient P in the region of the heart H. Using the EKG, it is possible retrospectively to select from recorded 2D X-ray projections those which have been recorded in a specific cardiac phase, in order to be able to reconstruct a high quality volume data set of the heart, free of motion artefacts in this specific cardiac phase using the selected 2D X-ray projections. The recording of the 2D X-ray projections and the recording of the EKG are in this case synchronized with one another, so that it is known in which cardiac phase a 2D X-ray projection has been recorded. The EKG signals are available to the computer 8 of the C-arm X-ray device 1 via a connection, not shown. This method for producing a volume data set is extremely appropriate if the heart H of the patient P has a relatively regular cardiac rhythm and a relatively regular cardiac frequency. In the case of a patient with cardiac arrhythmia, however, this method has been shown to be problematical in some cases.

Thus, according to the invention, it is proposed to arrange on the heart H of the patient P, for example on the coronary sinus, or at least indirectly, i.e. in the vicinity of the heart H, at least one X-ray positive electromagnetic sensor 13, which belongs to an electromagnetic position detection system 10. The sensor 13 may also be a catheter of the position detection system, which is placed and/or arranged in the heart, for example on the coronary sinus. The electromagnetic position detection system 10 comprises in addition to the electromagnetic sensor 13 a transmitter unit 11 arranged in a defined manner on the patient table 7, having in the case of the present embodiment three transmitters 12, which respectively generate an electromagnetic field. The transmitter unit 11 and the electromagnetic sensor 13 are connected to a computational device 14 of the electromagnetic position detection system 10, so that the sensor 13 is detected in the electromagnetic fields of the transmitters 12 and, in particular, the position thereof may be detected by the computational device 14 in a coordinate system CM assigned to the electromagnetic position detection system 10. Thus the positions of the electromagnetic sensor 13 and thus also the movements of the heart H may be detected.

In the case of the present embodiment, moreover, the patient P is provided with three X-ray positive electromagnetic body sensors 16 of the electromagnetic position detection system 10 arranged on the surface of the body of the patient P, the positions thereof also being able to be determined by the computational device 14 in the coordinate system CM assigned to the electromagnetic position detection system 10. For reasons of clarity, the connection of the body sensors 16 to the computational device 14 of the electromagnetic position detection system 10 is not included in the figures.

Moreover, each sensor 13 or 16 comprises three electromagnetic receiver units, so that the positions of the respective sensor may be determined by the position detection system in the three electromagnetic fields of the electromagnetic position detection system.

According to a first method, a plurality of 2D X-ray projections of the heart H from various projection directions are recorded by the C-arm X-ray device 1 by displacing the C-arm 2 about its orbital axis O by approximately 190° and thus around the heart H of the patient P. In these 2D X-ray projections, the X-ray positive electromagnetic sensor 13 and the X-ray positive electromagnetic body sensors 16 are also imaged.

The C-arm X-ray device 1 and the electromagnetic position detection system 10 are, moreover, registered with one another, which means that the C-arm X-ray device 1 and the electromagnetic position detection system 10 arranged in a defined manner on the patient table 7 are aligned in a defined manner with one another. The C-arm X-ray device 1 and the electromagnetic position detection system 10 are connected to one another via an interface 15 between the computer 8 and the computational device 14, via which the two devices may exchange, among other things, position data with one another. Thus alterations to the position of the C-arm X-ray device 1 or components of the C-arm X-ray device 1 are available to the electromagnetic position detection system 10 and alterations to the position of the electromagnetic position detection system 10 and/or positions of sensors of the electromagnetic position detection system 10 are available to the C-arm X-ray device 1.

Using the body sensors 16, which are substantially arranged at points of the surface of the body of the patient P which are at least substantially at rest, during the registering process a coordinate transformation is determined between an image coordinate system CB assigned to the C-arm X-ray device 1 and the coordinate system CM assigned to the electromagnetic position detection system 10. To this end, in the 2D X-ray projections the images of the body sensors 16 may be localized manually or even automatically by a method of pattern recognition and the coordinates thereof may be determined in the image coordinate system CB based on the known projection geometries of the C-arm X-ray device 1 contained in the projection matrices. Moreover, the coordinates of the electromagnetic body sensors 16 may be determined in the coordinate system CM assigned to the position detection system 10. Using the coordinates known in the two coordinate systems, the coordinate transformation may thus be determined by the computer 8 and/or the computational device 14. In this manner, the conditions are provided to superimpose images, for example, of the sensor 13 onto 2D X-ray projections or onto a volume data set reconstructed from the 2D X-ray projections.

Moreover, independently of the movements of the heart H, movements of the patient P during the recording of the 2D X-ray projections may be detected by means of the body sensors 16 and a relevant 2D X-ray projection may be corrected according to the movement of the patient P. A 2D X-ray projection affected by a movement of the patient P may, in this case, be determined based on a temporal synchronization, by the positions of the body sensors 16 being simultaneously detected over time at least during the recording of the 2D X-ray projections. As the time of the recording of each of the 2D X-ray projections is also known, in the case of a movement of the patient P, which is registered by an alteration to the position of the body sensors 16, a 2D X-ray projection affected by the movement of the patient P may be determined by a time comparison, and corrected according to the movement of the patient. The tissues of the patient P imaged in the relevant 2D X-ray projection are in this case shifted according to the movement of the patient P, as if the movement had not taken place.

In this manner, 2D X-ray projections of the heart H of the patient P are available to the computer 8 which, if the patient P has moved slightly during the recording of the 2D X-ray projections, are possibly corrected relative thereto.

In order to be able to reconstruct a volume data set of a specific cardiac phase of the heart H, the sensor 13 which has also been imaged in the 2D X-ray projections is detected in the individual 2D X-ray projections manually or automatically by means of a method of pattern recognition. To this end, for facilitating the identification of the sensor 13 in the individual 2D X-ray projections by taking into account the projection direction of a 2D X-ray projection and based on the position which the X-ray positive electromagnetic sensor 13 has adopted in this 2D X-ray projection, an image of the sensor 13 may be superimposed on the respective 2D X-ray projection in each, or even only in individual, 2D X-ray projections. This is possible due to the known coordinate transformation and the temporal synchronization between the recording of the 2D X-ray projections and the recording of the positions and/or the displacement curve of the sensor 13. Subsequently, a volume data set of the heart H of the patient P is reconstructed based on those 2D X-ray projections in which the X-ray positive electromagnetic sensor 13 adopts and/or has adopted a position characterizing a determined displacement phase of the heart H. The specific displacement phase or cycle phase of the heart H may, in this case, be established and/or determined using the displacement curve of the sensor 13 over time or even using additional reconstruction employing substantially all available 2D X-ray projections. In the additional reconstruction of the volume data set, the view of the heart is smudged, namely by motion artefacts. The volume data set as may be shown on the monitor 9, however, shows the trajectory and/or the displacement path 18 of the sensor 13, using which a cardiac phase may be selected for the reconstruction of the volume data set. In the case of the present embodiment, the uppermost extreme position 19 of the sensor 13 has been selected by way of example. Finally, based on this selection, the 2D X-ray projections are identified where, during the recording thereof, the sensor 13 has substantially adopted the uppermost extreme position 19. To this end, a specific interval may be allowed around the extreme position 19, which is selected so that practically no motion artefacts are present in the volume data set. The identified 2D X-ray projections are then used for the reconstruction of the cardiac phase selected using the extreme position 19, whereby a high quality volume data set of the heart H is obtained for this cardiac phase.

The X-ray projections for the reconstruction of the volume data set are selected by this method i.e. they are image based, which is why it may also be referred to as image-based gating or triggering.

Additionally, based on the positions of the X-ray positive electromagnetic sensor 13 and the 2D X-ray projections, in which the sensor 13 is imaged, and/or based on the electromagnetic body sensors 16 imaged in the 2D X-ray projections, the projection matrices of the C-arm X-ray device 1 may be determined by the computer 8 and compared with the projection matrices originally determined in a calibration process. This is possible due to the positions, which are known and/or which may be detected by the position detection system 10, of the sensor 13 and the body sensors 16 in the coordinate system assigned to the position detection system, so that the spatial positions of the sensors 13 and 16 are known and the parameters of the image geometries of the C-arm X-ray device 1 may be accurately determined. Preferably, in particular for determining the projection matrices again, more sensors 13 and 16 than those shown in FIG. 1 are used, therefore, which may be differentiated from one another in size, in order also to be able to differentiate the imaging thereof in 2D-X-ray projections from one another. Moreover, with regard to determining the projection geometries, reference is made by way of example to DE 101 40 867 B4, the method thereof being able to be applied in a corresponding manner in the present case for determining projection geometries.

Should deviations occur between recently determined and originally determined projection matrices, either the originally determined projection matrices are correspondingly corrected or only the recently determined projection matrices are used for the reconstruction of the volume data set of the heart H.

Moreover, there is the additional possibility of using as additional information the EKG signals recorded by the EKG device synchronously with the recording of the 2D X-ray projections and possibly using these EKG signals for selecting 2D X-ray projections if the cardiac rhythm of the patient is at least partially stable and does not exhibit arrhythmia.

As already mentioned, the positions of the sensor 13 are detected synchronously by the computational device 14 when obtaining the 2D X-ray projections and a displacement curve of the sensor 13 is generated therefrom, as is shown in FIG. 2.

Based on this displacement curve of the sensor 13 over time, according to a first alternative to the method a specific cardiac phase of the heart H of the patient P may be selected and a volume data set of the selected cardiac phase of the heart H of the patient P may be reconstructed based on those 2D X-ray projections, which have been recorded when the X-ray positive electromagnetic sensor 13 was located at a position characterizing the specific cardiac phase. The relevant 2D X-ray projections which have been recorded at the determined position of the sensor 13 at various projection angles, may be retrospectively selected from the plurality of recorded 2D X-ray projections by a time comparison.

Moreover, according to a second alternative to the method for reconstructing the volume data set, one may proceed in such a manner that based on constantly determined positions of the sensor 13 a cardiac phase corresponding to a specific position of the sensor 13 is selected and, only when the sensor 13 is located at the selected position, is a 2D X-ray projection obtained for the reconstruction of a volume data set of the selected cardiac phase. In this case, a 2D X-ray projection would always be triggered if the sensor 13 adopted a determined position. Also in this case, a displacement curve is plotted, as shown in FIG. 2. The cardiac phase is selected using the displacement curve.

In all three methods, the C-arm 2 is generally repeatedly, for example alternately, moved and/or pivoted about the patient P, in order to obtain 2D X-ray projections from various projection directions in the selected cardiac phase of the heart H of the patient P which is required for the reconstruction of the volume data set.

In the disclosed manner, a volume data set of the heart H of the patient P who suffers from cardiac arrhythmia, may accordingly be produced relative to a specific cardiac phase, which for example may be used for an ablation procedure. The electromagnetic position detection system may, therefore, at the same time also be a mapping system, in order to be able to obtain 3D mapping data of the heart H of the patient P.

The positions of the sensor 13 are determined at such time intervals that a displacement curve of the sensor 13 over time is obtained with sufficient temporal definition for selecting a specific cardiac phase.

In the case of the two last-disclosed alternative methods, the sensor 13 does not necessarily have to be X-ray positive or provided with an X-ray positive marker. If the sensor 13, however, is X-ray positive or is provided with an X-ray positive marker, this may be used for monitoring purposes. For example, using the reconstructed volume data set and the imaging of the sensor 13 in the volume data set in a manner which is free of artefacts, the correct selection and/or recording time of the 2D X-ray projections may be monitored.

Moreover, the sensor 13 imaged in the volume data set and the imaged body sensors 16 may be removed from the volume data set by image processing, for further use of the volume data set.

Moreover, the sensors 13 and, in particular, the body sensors 16 are arranged on the patient so that as far as possible said sensors do not overlay relevant structures of the heart H.

The three methods according to the invention, moreover, may also be combined in any manner with one another, in order to produce a volume data set of a mobile object to be examined.

The computer 8 and the computational device 14 have corresponding computer programs present in program memories, not shown, in order to execute the disclosed method. In this case, there is also the possibility of providing only one computer which operates both the C-arm X-ray device 1 and also the position detection system 10, and has the aforementioned computer programs. Provided that it is expedient, more than two computers may also be provided.

The invention has been explained above for obtaining a volume data set of the heart of a patient. The invention may, however, also be used for obtaining a volume data set of a different mobile tissue or organ, for example the lungs of a patient.

In this case, instead of an EKG device, a device may be used for recording the respiration cycle of the patient.

The invention claimed is:

1. A method for obtaining a volume data set of a mobile object of a patient by a C-arm X-ray device and an electromagnetic position detection system, comprising:
   arranging an electromagnetic sensor of the electromagnetic position detection system on the object;
   recording a plurality of X-ray projections of the object from various projection directions by the C-arm X-ray device;
   detecting the electromagnetic sensor in the X-ray projections; and
   reconstructing the volume data set from the X-ray projections in which the electromagnetic sensor corresponds to a position characterizing a determined displacement phase of the object.

2. The method as claimed in claim 1, wherein the electromagnetic sensor is detected by pattern recognition.

3. The method as claimed in claim 2, wherein the volume data set is reconstructed from the X-ray projections in which the electromagnetic sensor adopts the position characterizing the determined displacement phase of the object.

4. The method as claimed in claim 1, wherein the electromagnetic sensor is simultaneously detected by the electromagnetic position detection system when recording the X-ray projections.

5. The method as claimed in claim 4, wherein the volume data set is reconstructed from the X-ray projections in which the electromagnetic sensor is located in the position characterizing the determined displacement phase of the object.

6. The method as claimed in claim 1, wherein the electromagnetic sensor is detected by the electromagnetic position detection system.

7. The method as claimed in claim 6, wherein the X-ray projections are recorded only if the electromagnetic sensor is located in the position characterizing the determined displacement phase.

8. The method as claimed in claim 1, wherein the mobile object is a heart or lungs of the patient.

9. The method as claimed in claim 1, wherein the C-arm X-ray device is connected to the position detection system via an interface for exchanging position data with one another.

10. The method as claimed in claim 1, further comprising:
    arranging an electromagnetic body sensor on a surface of a body of the patient, wherein the electromagnetic body sensor is an X-ray positive electromagnetic body sensor or an electromagnetic body sensor provided with an X-ray position marker,
    detecting a movement of the patient by the electromagnetic body sensor, and
    correcting the X-ray projections recorded during the movement.

11. The method as claimed in claim 10, wherein the C-arm X-ray device and the electromagnetic position detection system are registered with one another.

12. The method as claimed in claim 11, wherein the registration comprises a determination of a coordinate transformation between an image coordinate system assigned to the C-arm X-ray device and a coordinate system assigned to the position detection system according to the electromagnetic body sensor.

13. The method as claimed in claim 11, wherein an image of the electromagnetic sensor is superimposed on the X-ray projections based on the projection directions and a position of the electromagnetic sensor.

14. The method as claimed in claim 10, wherein projection matrices of the C-arm X-ray device are redetermined based on a position of the electromagnetic sensor, the X-ray projections, and a position of the electromagnetic body sensor.

15. The method as claimed in claim 14, wherein the redetermined projection matrices are used for the reconstruction.

16. The method as claimed in claim 14,
    wherein projection matrices of the C-arm X-ray device that are determined previously are corrected by the redetermined projection matrices if alterations are detected, and
    wherein the corrected projection matrices are used for the reconstruction.

17. The method as claimed in claim 1, further comprising:
recording an EKG signal or data of respiration cycle of the patient, and
transmitting the EKG signal or the data of the respiration cycle to the C-arm X-ray device or the position detection system.

18. The method as claimed in claim 1, wherein the electromagnetic sensor is an X-ray positive electromagnetic sensor or an electromagnetic sensor provided with an X-ray position marker.

19. The method as claimed in claim 1, wherein the electromagnetic sensor is arranged indirectly on the object.

20. A device for reconstructing a volume data set of a mobile object of a patient, comprising:
a C-arm X-ray device that recodes a plurality of X-ray projections of the object from various projection directions;
an electromagnetic position detection system comprising an electromagnetic sensor that is arranged on the object; and
a computational device that reconstructs the volume data set from the X-ray projections in which the electromagnetic sensor corresponds to a position characterizing a determined displacement phase of the object.

* * * * *